United States Patent [19]

Money

[11] Patent Number: 4,513,212

[45] Date of Patent: Apr. 23, 1985

[54] AUTOMATIC P-WELL CLAMPING FOR CMOS INTEGRATED CIRCUIT

[75] Inventor: David K. Money, Pennant Hills, Australia

[73] Assignee: Electronics Pty. Ltd., Lane Cove, Australia

[21] Appl. No.: 401,012

[22] Filed: Jul. 22, 1982

[51] Int. Cl.³ .................. H03K 17/687; H03K 5/01; A61M 1/00

[52] U.S. Cl. .................. 307/575; 128/419 PG; 307/571; 307/568

[58] Field of Search .............. 307/575, 566, 568, 577, 307/579, 584, 585, 270, 571, 303

[56] References Cited

U.S. PATENT DOCUMENTS 4,274,014 6/1981 Schade, Jr. .................. 307/585
4,435,652 3/1984 Stevens ........................ 307/297

Primary Examiner—Stanley D. Miller
Assistant Examiner—B. P. Davis
Attorney, Agent, or Firm—Gottlieb, Rackman & Reisman

[57] ABSTRACT

A fast-operating, minimally complex circuit for automatically clamping the P wells of a CMOS integrated circuit to the most negative potential of the overall circuit. Each of a plurality of N-channel control transistors has its drain connected to a respective one of the circuit nodes whose potential may be the most negative at any given time. The source terminals of all of the control transistors are coupled to a common negative supply bus which is connected to all of the P wells in the integrated circuit. The gates of all of the control transistors are held at a potential which causes them to conduct drain-to-source current. If one of the nodes suddenly drops in potential, the respective control transistor conducts a current in the reverse direction which lowers the potential of the common bus to approximately the potential of the respective node. The respective control transistor conducts heavily until the common bus is thus clamped, and then conducts just enough current to maintain the clamping. Only a single control transistor is required for each node which may determine the most negative potential in the overall circuit. Rapid switching is enhanced by the substrate effect which comes into play when the current reverses direction in one of the control transistors and a large current flows. The same principle applies to integrated circuits containing N wells for P-channel transistors, and of course those containing both N wells and P wells.

24 Claims, 3 Drawing Figures

AUTOMATIC P-WELL CLAMPING FOR CMOS INTEGRATED CIRCUIT

This invention relates to the automatic clamping of P wells in a CMOS integrated circuit to the most negative potential in the circuit, and more particularly to such automatic P-well clamping as used in heart pacers. Similarly, it relates to CMOS processes utilizing N wells for the P-channel devices.

A CMOS P-channel device requires its source voltage to be positive with respective to its drain voltage. The N-type substrate of the device must be connected to a positive potential, usually the most positive in the overall circuit. An N-channel device, on the other hand, requires a source voltage which is negative with respect to its drain voltage. An N-channel device is normally made by first forming a P-well substrate in the N-type substrate, with two N-types regions then being diffused into the P well to serve as the source and drain. To maintain normal operation, the P well of an N-channel device must be connected to a negative potential, usually the most negative potential in the overall circuit.

There are many situations in which the most positive potential or the most negative potential can vary in magnitude. A typical example, that of a heart pacer, will be described below. The device is battery powered and the positive terminal of the battery serves as the reference voltage. Although the negative terminal of the battery may have a potential which is 2-3 volts more negative than the positive terminal, the most negative potential in the circuit may have a larger magnitude. This is because several mechanisms may exist for developing negative potentials which exceed the magnitude of the battery potential. It is well known, for example, that the battery voltage may be doubled in order to generate a pacing pulse.

While not all of the N-channel devices will require their P wells to be connected to the most negative potential, some of them may. The potential of any P well usually must be more negative than the potential of the source or drain. Since all of the P wells are usually connected together, proper operation of all N-channel devices can be assured simply by connecting all of the P wells to the most negative potential in the circuit.

In any circuit, it is generally known which nodes might possibly be at the most negative potential at one time or another. What is usually done is to provide a logic circuit for determining the node which is at the most negative potential in the circuit, and to couple the potential at this node to all of the P wells. There are three problems with prior art circuit arrangements. The first is that they are complex. The second is that they take too long to operate; when a new circuit node is suddenly placed at the most negative potential, some finite time is required before this negative potential is controlled by the logic circuit to be applied to all of the P wells. Until the switching is accomplished, one or more N-channel devices may have its source or drain at a potential which is more negative than that of the P well, and the device may conduct even though it should be held off. It is therefore important that when a new "most negative" potential is developed, that potential be applied to all of the P wells as fast as possible. The third problem is that prior art arrangements require prior knowledge of which node will be most negative.

It is a general object of my invention to provide a fast-operating, minimally complex automatic P-well clamping circuit for deriving a potential, for application to all of the P wells, which is equal to the most negative potential in the overall circuit.

At the outset, two things should be understood. The first is that my invention is not limited to CMOS integrated circuits. It is also applicable to integrated circuits which include only N-channel transistors where these are made by providing an N-type substrate with each N-channel transistor consisting of a P well having two N-type diffusions which serve as the source and drain. (Similary, the principles of my invention are applicable to the automatic clamping of the N-type wells to the most positive potential to assure proper operation of all P-channel devices where this type of technology is utilized.) The second point to note is that it is not necessary that the P wells be connected to a potential which actually equals the most negative potential in the overall circuit. What is important is that the P wells be connected to a potential which is greater than the most negative potential by less than the forward voltage drop of a PN junction. Each of the N-type source or drain diffusions, together with the P well, can function as a diode if the P well is more positive than the source or drain by a diode drop (0.6 volts). Erroneous operation will not ensue even if the P well is more positive in potential than the source or drain, provided that the P well is more positive than the source or drain potential by less than the forward voltage drop of a PN junction.

In accordance with the principles of my invention, I provide a single control transistor for each node whose potential might possibly become the most negative in the overall circuit. The source terminals of all of the control transistors are connected together on a common bus which serves as a negative supply bus in the sense that it is connected to all of the P wells in the overall circuit. A potential is applied to the gate of each of the control transistors causing it to conduct a low drain-to-source current. The drain of each of the control transistors is connected to a respective one of the nodes whose potential may become the most negative in the overall circuit. If the potential of any one of these nodes suddenly becomes the most negative, the respective control transistor conducts a momentary large source-to-drain current which lowers the potential of the negative supply bus to a value which is greater than the potential at the respective node by less than the forward voltage drop of a PN junction. Thus the potential on the negative supply bus is controlled by the new node which is now at the most negative potential in the overall circuit.

Further objects, features and advantages of my invention will become apparent upon consideration of the following detailed description in conjunction with the drawing, in which.

Figure 1:
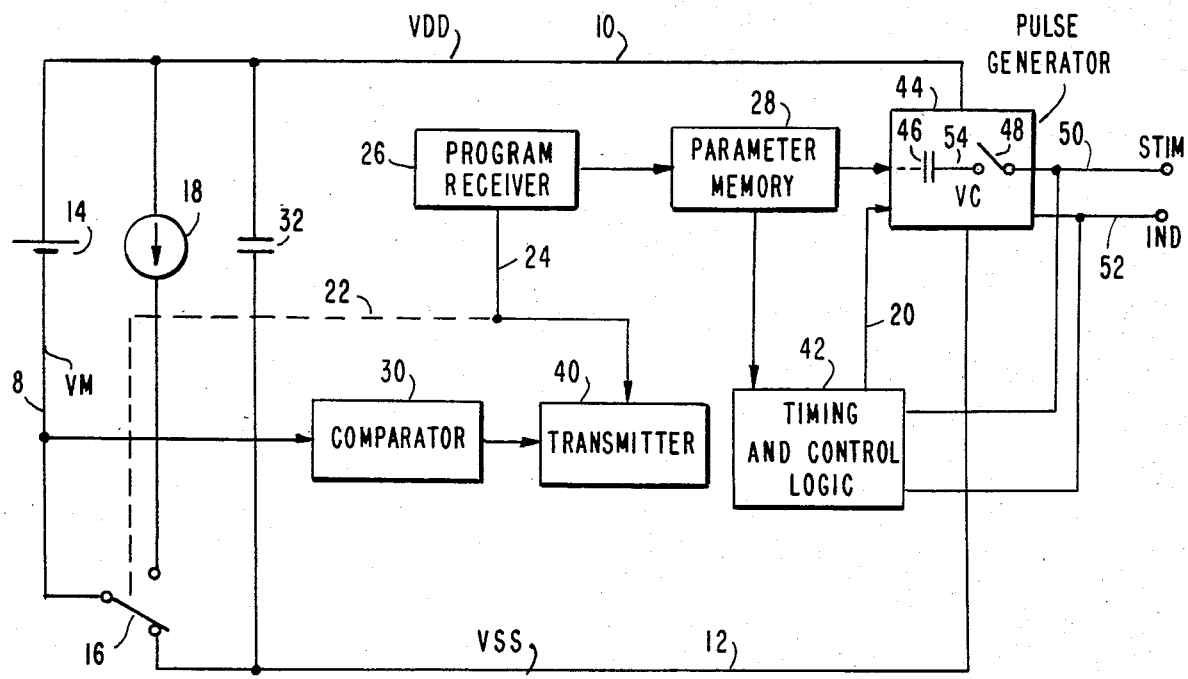
FIG. 1 depicts symbolically a typical heart pacer circuit which will be helpful in understanding the need for an automatic P-well clamping circuit.

In the heart pacer of FIG. 1, the positive terminal of battery 14 is connected to bus 10. The potential of this bus is VDD and it serves as the reference potential for the overall circuit. The negative terminal of the battery is connected to conductor 8, whose potential is VM. Switch 16 is normally in the position shown, with conductor 8 being connected to conductor 12. The potential VSS on conductor 12 is the negative supply potential which powers the several blocks in the system. Capacitor 32 is the usual filter capacitor for limiting the effects of transients on the VDD and VSS potentials.

Program receiver 26 is a conventional device which responds to externally-generated signals for controlling the pacer operation. Depending upon the particular code transmitted by an external programmer under control of the physician, several different parameter values may be stored in memory 28. These parameter values control such things as pacer rate, pulse amplitude, pulse width, etc.

Pulse generator 44 is the device which controls the application of a current pulse over leads 50, 52 which are connected respectively to the stimulating and indifferent electrodes. Following the generation of a stimulating pulse, capacitor 46 charges and a negative potential VC is developed on conductor (node) 54. When switch 48 closes, potential VC appears on the stimulating electrode lead 50. The indifferent electrode lead 52 is connected to potential bus 10, and current flows over the two leads and through the patient's heart. The manner in which a potential is developed on capacitor 46 is not important for an understanding of the present invention. Reference may be made in this regard to my copending applications Ser. No. 251,191, entitled "Voltage Multiplier for Implantable Tissue Stimulator" filed on Apr. 6, 1981, and Ser. No. 251,192, entitled "Direct-Coupled Output Stage For Rapid-Signal Biological Stimulator" filed on Apr. 6, 1981, both of which applications are hereby incorporated by reference. The important point to note here is that potential VC may equal negative potential VSS, or it may be considerably larger in magnitude.

Parameter memory 28 controls the operation of pulse generator 24 in that it determines the pulse amplitude. When a stimulating pulse is actually generated is determined by timing and control logic 42. Two inputs to this circuit are connected to the electrode leads so that spontaneous heart activity can be sensed. The timing and control logic operates in accordance with parameter values stored in memory 28; for example, depending upon the pacing rate selected by the physician, the timing and control logic determines when an excessive time has gone by since the last heartbeat. When the timing and control logic determines that a stimulating pulse is required, it momentarily pulses conductor 20 high to trigger operation of the pulse generator. The duration of the pulse is determined by the pulse-width parameter value stored in memory 28.

Many conventional heart pacers are provided with test circuits for allowing the open-circuit potential and internal impedance of the battery to be ascertained; toward the end of life of the pacer, the battery impedance increases and it is certainly advantageous for the physician to be informed of the need for an impending replacement. The open-circuit potential and "end-of-life" tests are shown symbolically only, the details not being necessary for an understanding of the present invention. Reference may be made in this regard to my copending application Ser. No. 401,013, entitled "Heart Pacer End-Of-Life Detector" filed on July 22, 1982, and hereby incorporated by reference. When program receiver 26 determines that the end-of-life test is to be performed, a control signal is applied to conductor 24. This signal in turn causes switch 16 to connect current source 18 across battery 14, as shown symbolically by dashed line 22. (During the test, the pacer is still powered by the potential which appears across filter capacitor 32.) The signal on conductor 24 also turns on transmitter 40.

As current from source 18 flows through switch 16 and up through battery 14, the potential VM becomes less negative due to the drop across the internal impedance of battery 14. The potential VM is compared to a threshold level by comparator 30, and the results of the comparison are furnished to transmitter 40. The transmitter transmits a signal to an external monitor which indicates whether the potential VM is too low in magnitude, indicating the approach of an end-of-life condition.

The open-circuit potential test is controlled by program receiver 26 causing switch 16 to assume a neutral position, connecting conductor 8 to neither the current source or the VSS bus. As soon as current ceases to flow through the battery, potential VM falls. Once again, comparator 30 performs an appropriate test and controls the transmission of a corresponding signal to an external monitor.

The system of FIG. 1 is included herein only in order to show the manner in which the most negative potential in an overall circuit may appear at different nodes at different times. Conductor 12 is the negative supply bus and is held at a potential VSS. The negative potential VC on conductor 54 is not necessarily of the largest magnitude. In the event the pacer employs a voltage doubler for charging capacitor 46 to twice the supply potential, potential VC will certainly exceed potential VSS in magnitude prior to the generation of a pacing pulse. But during the course of the pacing pulse, potential VC may fall below potential VSS as capacitor 46 discharges. Also, if the pacer is programmed to give an output voltage equal to or less than VSS, then VC will be less negative than VSS. As for potential VM, it is normally less than potential VSS in magnitude. However, during the open-circuit potential test, the magnitude of potential VM will usually exceed the magnitude of potential VSS.

Figure 2:
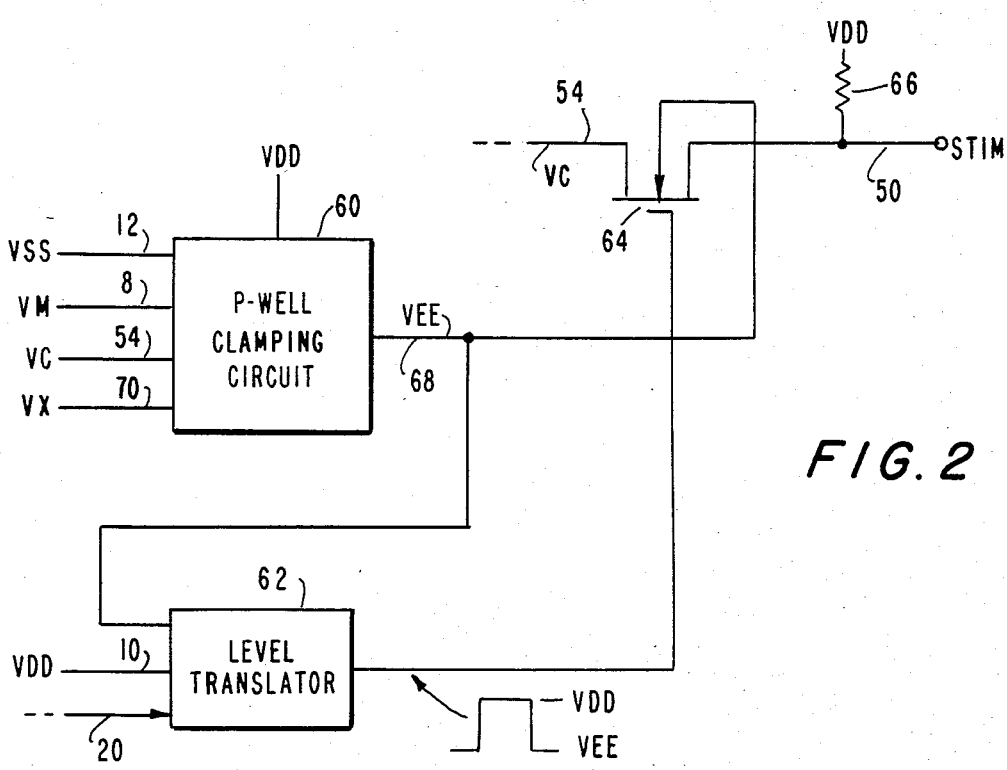
FIG. 2 depicts the manner in which the P-well clamping circuit of my invention can be used in the heart pacer of FIG. 1.

The circuit of FIG. 2 illustrates the P-well clamping circuit of my invention as block 60, and it also further depicts some details of a typical heart pacer. In this figure, switch 48 of FIG. 1 is replaced by N-channel transistor 64. Potential VC on conductor 54 is applied to the source of the transistor, and the drain of the transistor is returned through resistor 66 to the reference supply bus. When the transistor is turned on with the application of a positive potential to its gate with respect to its source, current from capacitor 46 is extended over lead 50 to the stimulating electrode. Two connections to transistor 64 are important. The first is the gate connection which determines whether the transistor is held on or off. The second is the substrate connection to which is applied a potential VEE at the output of block 60; as described above, potential VEE should not exceed the source potential of transistor 64 by more than about 0.6 volts if the transistor is to be held off by a negative potential at its gate. The function of the P-well clamping circuit is to derive a voltage VEE which is equal to the most negative potential in the overall circuit. This voltage VEE is applied to the P wells of all N-channel transistors in the circuit, of which transistor 64 is only one example. By causing potential VEE to approximate the most negative potential in the overall circuit, the same negative supply bus can be used to bias all of the P wells.

Four inputs are shown to the P-well clamping circuit. Three of these inputs are the VSS, VM and VC potentials described in connection with FIG. 1. The VX potential input on conductor 70 simply represents some other node in the system of FIG. 1 which on occasion might represent the most negative potential in the system. The function of circuit 50 is to derive a potential VEE which approximates the most negative of the four input potentials to the extend that potential VEE is higher than the most negative potential input by less than a forward voltage drop of a PN junction.

Level translator 62, part of the pulse generator block 44 of FIG. 1, is a conventional circuit for controlling the switching of transistor 64. The level translator has two inputs, one of which is coupled to the output depending on the state of control line 20. One of the two inputs is the reference supply potential VDD on bus 10. The other is the most negative potential VEE which is derived by P-well clamping circuit 60. Conductor 20 is high in potential when pacing current is to flow and transistor 64 is to conduct; a high potential on conductor 20 causes level translator 62 to apply the VDD input potential to the gate of transistor 64. When control conductor 20 is low in potential, potential VEE is extended to the gate of transistor 64 to hold it off. By using potential VEE as one of the inputs to the level translator, it can be assured that the transistor will be held off when it should be held off since potential VEE is the most negative potential available.

Figure 3:
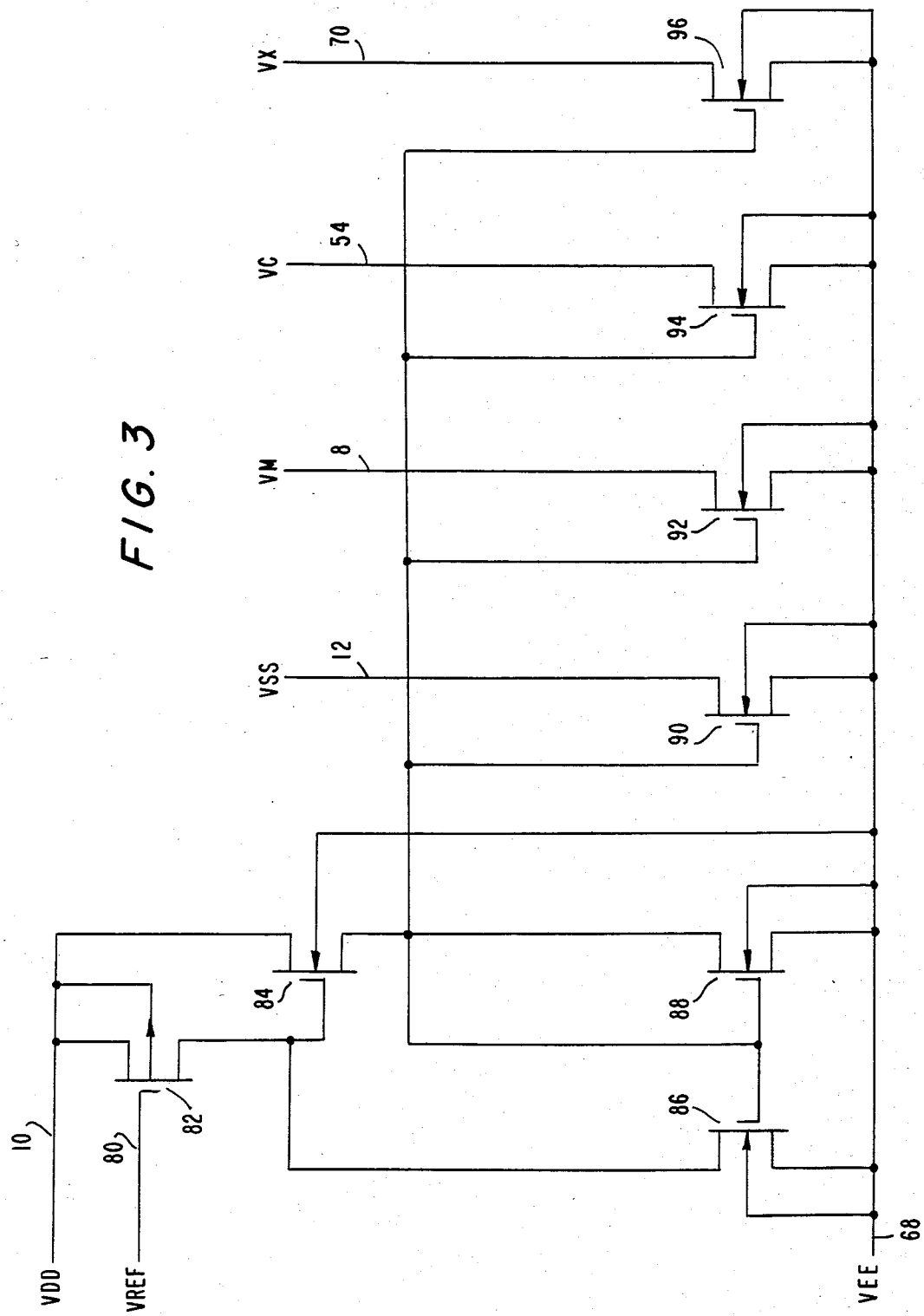
FIG. 3 is the illustrative embodiment of the invention and depicts the detailed circuitry which is included in block 60 of FIG. 2.

Before proceeding to a description of FIG. 3, another aspect of the operation of the circuit of FIG. 1 should be considered. In an actual pacer implementation, switch 16 would comprise two or more N-channel transistors. Consider a single one of these transistors which connects conductors 8 and 12 to each other, with this transistor normally conducting but being turned off when one of the two tests is performed. (Another transistor would be provided for selectively connecting conductor 8 to current source 18.) When the open-circuit potential test is being performed, it is not wise to apply potential VSS to the gate of the transistor which connects conductors 8 and 12 in order to turn the transistor off. The reason for this is that voltage VM becomes more negative when current ceases to flow through the battery. If voltage VM decreases below the gate voltage VSS by more than a gate threshold, the transistor would turn on again with the terminal connected to the battery serving as the source. In such a case, it would not be possible to measure the open-circuit potential. It might be thought that the potential at the negative terminal of the battery could itself be applied to the gate of the transistor when it is necessary to hold the transistor off. However, when current source 18 is connected across the battery in order to test its internal impedance, voltage VM rises. In such a case, the transistor would certainly be turned on. Thus the only effective way to ensure that the transistor which connects conductors 8 and 12 to each other is held off when it is to be held off, under all circumstances, is to apply the most negative potential in the circuit to its gate. The same potential VEE which is derived by the P-well clamping circuit 60 can be used for this purpose.

Referring to FIG. 3 and comparing it to block 60 of FIG. 2, it will be seen that they both have the same inputs and outputs. Potential VDD is the reference or ground potential for the circuit. The potential on bus 68 is VEE, and it is made equal to the most negative of the four input potentials VSS, VM, VC and VX. The only additional input on FIG. 3 is a reference potential VREF applied to conductor 80. This potential is simply a reference potential for controlling the current flow through transistor 82. Any of conventional circuits for deriving a reference potential may be utilized, although a preferred circuit is that disclosed in application Ser. No. 237,089, entitled "Monitorable Bone Growth Stimulator" filed on Feb. 23, 1981, which application is hereby incorporated by reference.

Transistors 82, 84 and 88 are designed to control a current flow of 100 nanoamperes through transistor 86. Transistors 84 and 88 constitute a feedback network to control this preset current flow. Transistor 82 serves as a current source of 100 nanoamperes with substantially all of the current flowing through transistor 86. If the current through transistor 86 tends to decrease, the voltage at the gate of transistor 84 increases, this transistor conducts more heavily, and the gate of transistor 86 goes more positive to control a larger current flow through transistor 86. Similar remarks apply if the current through transistor 86 tends to increase. The net result is that transistors 84 and 88 control a constant current of 100 nanoamperes to flow through transistor 86. Because the gates of control transistors 90, 92, 94 and 96 are all connected to the gate of transistor 86, the former transistors can function as current mirrors each to conduct 100 nanoamperes if the geometries of transistors 86, 90, 92, 94 and 96 are the same.

Of the four transistors 90, 92, 94 and 96, the current mirror relationship applies only if the drains of the transistors are significantly more positive than the sources connected to negative bus 68. One of the transistors is connected to the most negative potential, and controls bus 68 to assume a potential only slightly higher; thus this one of the control transistors sinks to this most negative potential all the current sourced to bus 68 by conducting in the opposite direction, as will now be described.

Suppose that potential VC, for example, suddenly becomes the most negative potential. The upper terminal of transistor 94 which was previously functioning as a drain now acts as a source since potential VC is more negative than potential VEE. The transistor can conduct heavily (many microamperes), to charge the nodal capacitance on bus 68 to the new voltage, because the potential difference between the gate and the new source is much higher than the potential difference between the gate and the old source (connected to bus 68). Conduction prior to potential VC going very negative was controlled by a gate-source potential which just exceeded the threshold voltage (as determined by the gate-source potential of transistor 86 which conducts 100 nanoamperes); now, however, the drive is significantly higher and transistor 94 conducts quite heavily with conductor 68 being returned through the transistor to conductor 54, potential VEE thus approximating potential VCC. Potential VEE is more positive than potential VC, but only by about 100-150 millivolts in a typical case when conducting the 0.5 to 1 milliamperes or so typically required, i.e., the sum of the currents into bus 68.

Once potential VEE is thus pulled down, the gate of transistor 86 also drops because its potential exceeds that of potential VEE by about the threshold level of the transistor. Because the gate of transistor 86 is connected to the gate of each of transistors 90, 92, 94 and 96, the gate potentials of all of these devices similarly drop to a level which is about one threshold above level VEE. Consequently, each of transistors 90, 92 and 96 continues to conduct about 100 nanoamperes. It is only the three other transistors which have source potentials which are much larger than their drain potentials and conduct mirrored currents. Transistor 94 conducts relatively little current after the initial surge, in the opposite direction—just enough to maintain potential VEE at the most negative level while sinking the sum of the currents into bus 68.

The threshold voltage is the potential between the gate and source of a field-effect transistor which is required for conduction to begin. The threshold voltage for an N-channel device, as the term is normally used, assumes that the P well is connected to the source of the device. If the P well is connected to a more negative potential the threshold voltage increases, and if it is connected to a more positive potential the threshold voltage is lowered. In the example considered above, in which transistor 94 is the one which causes potential VEE to be lowered to potential VC, when potential VC first drops and current flow through transistor 94 reverses in direction, it will be noted that the P well of the device is now connected to the effective drain which is at potential VEE, which potential is higher than potential VC. Thus the threshold voltage is lowered and reverse conduction in transistor 94 is enhanced. The effect, which is known as the "substrate effect", assists clamping of bus 68 to the most negative of the four input potentials.

The circuit is fast operating for yet another reason. Due to the inherent drain-gate capacitance of transistor 94 (or any of the other three transistors when it controls the potential on bus 68), an instantaneous drop in drain potential on conductor 54 is reflected in an instantaneous drop in gate potential. Since the gates of all of transistors 90, 92, 94 and 96 are connected to the source of transistor 84, when potential VC drops suddenly the gate-source drop across transistor 84 increases rapidly and transistor 84 is driven harder. This, in turn, causes transistor 94 to be driven harder, with current now flowing in the upward direction as described above.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. An integrated circuit having field-effect transistors comprising a plurality of N-channel transistors each having a P-well, source and drain terminals, and a gate terminal; a source of potential for powering all of said transistors; a plurality of nodes having potentials derived thereon, each of which may be the most negative potential in the integrated circuit at any given time; and a negative supply bus connected to all of said P-wells; characterized by a plurality of control transistors each having its drain terminal coupled to a respective one of said nodes; the source terminals of all of said control transistors being coupled to said negative supply bus; and means for applying a potential to the gate terminal of each of said control transistors to cause it to conduct a drain-to-source current; that one of the control transistors whose drain is at the most negative potential conducting a source-to-drain current to lower the potential of said negative supply bus to a value which is greater than said most negative potential by less than the forward voltage drop of a PN junction.

2. An integrated circuit having field-effect transistors in accordance with claim 1 further including means for selectively controlling the turning off of at least one of said plurality of N-channel transistors by applying the potential on said negative supply bus to the gate terminal thereof.

3. An integrated circuit having field-effect transistors in accordance with claim 2 wherein said plurality of N-channel transistors are arranged to function as a heart pacer; said heart pacer including a negative power rail, and a capacitor for charging and then generating a pacing pulse and having a point of maximum negative potential therein; at least two of said nodes having applied respectively thereto the potential of said negative rail and the potential of said point of maximum negative potential.

4. An integrated circuit having field-effect transistors in accordance with claim 3 wherein said means for causing each of said control transistors to conduct a drain-to-source current includes a current-mirror circuit.

5. An integrated circuit having field-effect transistors in accordance with claim 4 further including means for controlling a substrate effect in the control transistor which conducts a source-to-drain current when the potential of the node coupled to the drain terminal of such transistor first becomes the most negative in the integrated circuit, to cause enough source-to-drain current to flow until said negative supply bus is clamped to the most negative potential at said node.

6. An integrated circuit having field-effect transistors in accordance with claim 2 wherein said means for causing each of said control transistors to conduct a drain-to-source current includes a current-mirror circuit.

7. An integrated circuit having field-effect transistors in accordance with claim 6 further including means for controlling a substrate effect in the control transistor which conducts a source-to-drain current when the potential of the node coupled to the drain terminal of such transistor first becomes the most negative in the integrated circuit, to cause enough source-to-drain current to flow until said negative supply bus is clamped to the most negative potential at said node.

8. An integrated circuit having field-effect transistors in accordance with claim 2 further including means for controlling a substrate effect in the control transistor which conducts a source-to-drain current when the potential of the node coupled to the drain terminal of such transistor first becomes the most negative in the integrated circuit, to cause enough source-to-drain current to flow until said negative supply bus is clamped to the most negative potential at said node.

9. An integrated circuit having field-effect transistors in accordance with claim 1 wherein said plurality of N-channel transistors are arranged to function as a heart pacer; said heart pacer including a negative power rail, and a capacitor for charging and then generating a pacing pulse and having a point of maximum negative potential therein; at least two of said nodes having applied respectively thereto the potential of said negative rail and the potential of said point of maximum negative potential.

10. An integrated circuit having field-effect transistors in accordance with claim 1 wherein said means for causing each of said control transistors to conduct a drain-to-source current includes a current-mirror circuit.

11. An integrated circuit having field-effect transistors in accordance with claim 10 further including means for controlling a substrate effect in the control transistor which conducts a source-to-drain current when the potential of the node coupled to the drain terminal of such transistor first becomes the most negative in the integrated circuit, to cause enough source-to-drain current to flow until said negative supply bus is clamped to the most negative potential at said node.

12. An integrated circuit having field-effect transistors in accordance with claim 1 further including means for controlling a substrate effect in the control transistor which conducts a source-to-drain current when the potential of the node coupled to the drain terminal of such transistor first becomes the most negative in the integrated circuit, to cause enough source-to-drain current to flow until said negative supply bus is clamped to the most negative potential at said node.

13. An integrated circuit having field-effect transistors comprising a plurality of transistors each having a substrate, source and drain terminals, and a gate; a source of potential for powering all of said transistors; a plurality of nodes having potentials of the same polarity derived thereon, each of which may be of the largest magnitude in the integrated circuit at any given time; and a common supply bus connected to all of said substrates; characterized by a plurality of control transistors each having its terminal of one type coupled to a respective one of said nodes; the terminals of the other type of all of said control transistors being coupled to said common supply bus; and means for applying a potential to the gate of each of said control transistors to cause it to conduct a current in a first direction; that one of the control transistors whose terminal of said one type is at the potential of largest magnitude conducting current in a second direction to clamp said common supply bus to said potential of largest magnitude.

14. An integrated circuit having field-effect transistors in accordance with claim 13 further including means for selectively controlling the turning off of at least one of said plurality of transistors by applying the potential on said common supply bus to the gate terminal thereof.

15. An integrated circuit having field-effect transistors in accordance with claim 14 wherein said plurality of N-channel transistors are arranged to function as a heart pacer; said heart pacer including a negative power rail, and a capacitor for charging and then generating a pacing pulse and having a point of maximum negative potential therein; at least two of said nodes having applied respectively thereto the potential of said negative rail and the potential of said point of maximum negative potential.

16. An integrated circuit having field-effect transistors in accordance with claim 15 wherein said means for causing each of said control transistors to conduct a current in said first direction includes a current-mirror circuit.

17. An integrated circuit having field-effect transistors in accordance with claim 16 further including means for controlling a substrate effect in the control transistor which conducts a current in said second direction when the potential of the node coupled to the terminal of said one type of such transistor first assumes the largest magnitude in the integrated circuit, to cause enough current in said second direction to flow until said supply bus is clamped to the potential of largest magnitude at said node.

18. An integrated circuit having field-effect transistors in accordance with claim 14 wherein said means for causing each of said control transistors to conduct a current in said first direction includes a current-mirror circuit.

19. An integrated circuit having field-effect transistors in accordance with claim 18 further including means for controlling a substrate effect in the control transistor which conducts a current in said second direction when the potential of the node coupled to the terminal of said one type of such transistor first assumes the largest magnitude in the integrated circuit, to cause enough current in said second direction to flow until said supply bus is clamped to the potential of largest magnitude at said node.

20. An integrated circuit having field-effect transistors in accordance with claim 14 further including means for controlling a substrate effect in the control transistor which conducts a current in said second direction when the potential of the node coupled to the terminal of said one type of such transistor first assumes the largest magnitude in the integrated circuit, to cause enough current in said second direction to flow until said supply bus is clamped to the potential of largest magnitude at said node.

21. An integrated circuit having field-effect transistors in accordance with claim 13 wherein said plurality of N-channel transistors are arranged to function as a heart pacer; said heart pacer including a negative power rail, and a capacitor for charging and then generating a pacing pulse and having a point of maximum negative potential therein; at least two of said nodes having applied respectively thereto the potential of said negative rail and the potential of said point of maximum negative potential.

22. An integrated circuit having field-effect transistors in accordance with claim 13 wherein said means for causing each of said control transistors to conduct a current in said first direction includes a current-mirror circuit.

23. An integrated circuit having field-effect transistors in accordance with claim 22 further including means for controlling a substrate effect in the control transistor which conducts a current in said second direction when the potential of the node coupled to the terminal of said one type of such transistor first assumes the largest magnitude in the integrated circuit, to cause enough current in said second direction to flow until said supply bus is clamped to the potential of largest magnitude at said node.

24. An integrated circuit having field-effect transistors in accordance with claim 13 further including means for controlling a substrate effect in the control transistor which conducts a current in said second direction when the potential of the node coupled to the terminal of said one type of such transistor first assumes the largest magnitude in the integrated circuit, to cause enough current in said second direction to flow until said supply bus is clamped to the potential of largest magnitude at said node.

* * * * *